United States Patent
Sadaka

(10) Patent No.: US 9,451,929 B2
(45) Date of Patent: Sep. 27, 2016

(54) DEGASSING INTRAVASCULAR ULTRASOUND IMAGING SYSTEMS WITH SEALED CATHETERS FILLED WITH AN ACOUSTICALLY-FAVORABLE MEDIUM AND METHODS OF MAKING AND USING

(75) Inventor: Alain Sadaka, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1136 days.

(21) Appl. No.: 12/425,191

(22) Filed: Apr. 16, 2009

(65) Prior Publication Data

US 2009/0264769 A1  Oct. 22, 2009

Related U.S. Application Data

(60) Provisional application No. 61/045,904, filed on Apr. 17, 2008.

(51) Int. Cl.
| | |
|---|---|
| *A61B 8/14* | (2006.01) |
| *A61B 8/12* | (2006.01) |
| *A61B 8/08* | (2006.01) |
| *A61B 8/00* | (2006.01) |

(52) U.S. Cl.
CPC .............. *A61B 8/12* (2013.01); *A61B 8/0833* (2013.01); *A61B 8/4281* (2013.01); *A61B 8/445* (2013.01)

(58) Field of Classification Search
USPC ............... 600/115, 439, 463, 470; 156/173; 604/10, 509, 97.02, 97.03, 99.03; 606/159, 200, 94
See application file for complete search history.

(56) References Cited

U.S. PATENT DOCUMENTS

| | | | |
|---|---|---|---|
| 4,043,181 A | 8/1977 | Nigam | |
| 4,057,049 A | 11/1977 | Hill et al. | |
| 4,063,549 A | 12/1977 | Beretsky et al. | |
| 4,350,917 A | 9/1982 | Lizzi et al. | |
| 4,484,569 A * | 11/1984 | Driller et al. | ............ 600/439 |

(Continued)

FOREIGN PATENT DOCUMENTS

| | | |
|---|---|---|
| EP | 0 459 813 A2 | 12/1991 |
| JP | 6-047045 A | 2/1994 |

(Continued)

OTHER PUBLICATIONS

International Search Report and Written Opinion for International Patent Application No. PCT/2009/046348 mailed Oct. 20, 2010.

(Continued)

*Primary Examiner* — Serkan Akar
(74) *Attorney, Agent, or Firm* — Lowe Graham Jones PLLC; Bruce E. Black

(57) ABSTRACT

A catheter assembly for an intravascular ultrasound system includes a catheter and an imaging core. The catheter has a longitudinal length, a distal end, and a proximal end. The catheter includes a sealable lumen extending along the longitudinal length of the catheter from the proximal end to the distal end, and a movable plunger or a movable seal in fluid communication with the lumen. The movable plunger or the movable seal provides a gas-tight seal. The movable plunger or the movable seal is configured and arranged for adjusting to changes in volume of the lumen when the lumen is filled with an acoustically-favorable medium and sealed. The imaging core is configured and arranged for inserting into the sealable lumen and for coupling to a control module.

2 Claims, 6 Drawing Sheets

(56) References Cited

U.S. PATENT DOCUMENTS

| | | | |
|---|---|---|---|
| 4,550,607 A | 11/1985 | Maslak et al. | |
| 4,561,019 A | 12/1985 | Lizzi et al. | |
| 4,662,380 A | 5/1987 | Riley | |
| 4,817,015 A | 3/1989 | Insana et al. | |
| 4,858,124 A | 8/1989 | Lizzi et al. | |
| 4,932,414 A | 6/1990 | Coleman et al. | |
| 4,945,478 A | 7/1990 | Merickel et al. | |
| 4,951,677 A * | 8/1990 | Crowley et al. | 600/463 |
| 4,982,339 A | 1/1991 | Insana et al. | |
| 5,016,615 A | 5/1991 | Driller et al. | |
| 5,125,410 A | 6/1992 | Misono et al. | |
| 5,167,233 A * | 12/1992 | Eberle et al. | 600/470 |
| 5,193,546 A * | 3/1993 | Shaknovich | 600/463 |
| 5,224,480 A | 7/1993 | Yamada et al. | |
| 5,257,624 A | 11/1993 | Fraser et al. | |
| 5,293,871 A | 3/1994 | Reinstein et al. | |
| 5,331,947 A * | 7/1994 | Shturman | 600/115 |
| 5,335,184 A | 8/1994 | Hildebrand | |
| 5,350,390 A * | 9/1994 | Sher | 606/159 |
| 5,375,470 A | 12/1994 | Matsushima et al. | |
| 5,381,385 A | 1/1995 | Greenstein | |
| 5,417,215 A | 5/1995 | Evans et al. | |
| 5,477,858 A | 12/1995 | Norris et al. | |
| 5,485,845 A | 1/1996 | Verdonk et al. | |
| 5,501,221 A | 3/1996 | Foster et al. | |
| 5,579,768 A | 12/1996 | Klesenski | |
| 5,640,961 A | 6/1997 | Verdonk | |
| 5,792,058 A | 8/1998 | Lee et al. | |
| 5,967,984 A | 10/1999 | Chu et al. | |
| 6,039,689 A | 3/2000 | Lizzi | |
| 6,050,947 A | 4/2000 | Rhyne et al. | |
| 6,095,976 A | 8/2000 | Nachtomy et al. | |
| 6,102,859 A | 8/2000 | Mo | |
| 6,120,445 A | 9/2000 | Grunwald | |
| 6,120,446 A | 9/2000 | Ji et al. | |
| 6,142,940 A | 11/2000 | Lathbury et al. | |
| 6,154,560 A | 11/2000 | Cothren et al. | |
| 6,159,153 A | 12/2000 | Dubberstein et al. | |
| 6,186,951 B1 | 2/2001 | Lizzi et al. | |
| 6,238,342 B1 | 5/2001 | Feleppa et al. | |
| 6,263,094 B1 | 7/2001 | Rosich et al. | |
| 6,287,259 B1 | 9/2001 | Grunwald | |
| 6,312,383 B1 | 11/2001 | Lizzi et al. | |
| 6,413,222 B1 * | 7/2002 | Pantages et al. | 600/466 |
| 6,423,007 B2 | 7/2002 | Lizzi et al. | |
| 6,514,202 B2 | 2/2003 | Grunwald | |
| 6,579,238 B1 | 6/2003 | Simopoulos et al. | |
| 6,592,520 B1 | 7/2003 | Peszynski et al. | |
| 6,621,341 B1 | 9/2003 | Shifrin | |
| 6,743,174 B2 | 6/2004 | Ng et al. | |
| 6,758,818 B2 * | 7/2004 | Pantages et al. | 600/466 |
| 6,945,938 B2 | 9/2005 | Grunwald | |
| 7,306,561 B2 | 12/2007 | Sathyanarayana | |
| 7,780,599 B2 * | 8/2010 | Nierich | 600/443 |
| 7,806,856 B2 * | 10/2010 | Bagaoisan et al. | 604/97.03 |
| 8,038,682 B2 * | 10/2011 | McGill et al. | 606/94 |
| 2002/0087218 A1 | 7/2002 | Amemiya | |
| 2002/0151799 A1 * | 10/2002 | Pantages et al. | 600/466 |
| 2003/0023393 A1 | 1/2003 | Oravecz | |
| 2003/0083547 A1 * | 5/2003 | Hamilton et al. | 600/116 |
| 2004/0002435 A1 | 1/2004 | Petersen et al. | |
| 2004/0006273 A1 | 1/2004 | Kim et al. | |
| 2004/0039286 A1 | 2/2004 | Kuban et al. | |
| 2004/0039305 A1 * | 2/2004 | Eberhart et al. | 600/585 |
| 2004/0193051 A1 * | 9/2004 | Mandrusov et al. | 600/439 |
| 2006/0100522 A1 | 5/2006 | Yuan et al. | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |
| 2008/0009794 A1 * | 1/2008 | Bagaoisan et al. | 604/104 |
| 2008/0041516 A1 * | 2/2008 | Chiu et al. | 156/173 |
| 2008/0103478 A1 * | 5/2008 | Chiu et al. | 604/509 |
| 2008/0103523 A1 * | 5/2008 | Chiu et al. | 606/200 |
| 2009/0005733 A1 * | 1/2009 | Chiu et al. | 604/99.01 |
| 2009/0018498 A1 * | 1/2009 | Chiu et al. | 604/97.02 |
| 2009/0264769 A1 * | 10/2009 | Sadaka | 600/463 |
| 2010/0113968 A1 * | 5/2010 | Bobo et al. | 600/561 |

FOREIGN PATENT DOCUMENTS

| | | |
|---|---|---|
| WO | WO-92/01932 | 2/1992 |
| WO | WO-94/23652 | 10/1994 |
| WO | WO-96/28096 | 9/1996 |
| WO | WO-01/82787 A2 | 11/2001 |
| WO | WO-03/083506 A1 | 10/2003 |
| WO | 2004/021404 A2 | 3/2004 |
| WO | 2007/099746 A1 | 9/2007 |

OTHER PUBLICATIONS

International Preliminary Report on Patentability for International Patent Application No. PCT/US2009/046348 mailed Oct. 28, 2010.

* cited by examiner

US 9,451,929 B2

DEGASSING INTRAVASCULAR ULTRASOUND IMAGING SYSTEMS WITH SEALED CATHETERS FILLED WITH AN ACOUSTICALLY-FAVORABLE MEDIUM AND METHODS OF MAKING AND USING

CROSS REFERENCE TO RELATED APPLICATION

This application claims the benefit of U.S. Provisional Patent Application Ser. No. 61/045,904, filed Apr. 17, 2008, the entire contents of which is incorporated by reference.

TECHNICAL FIELD

The present invention is directed to the area of intravascular ultrasound imaging systems and methods of making and using the systems. The present invention is also directed to an intravascular ultrasound imaging system with a catheter having a sealed lumen filled with an acoustically-favorable medium, as well as methods of making and using the intravascular ultrasound systems.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

In one embodiment, a catheter assembly for an intravascular ultrasound system includes a catheter and an imaging core. The catheter has a longitudinal length, a distal end, and a proximal end. The catheter includes a sealable lumen extending along the longitudinal length of the catheter from the proximal end to the distal end, and a movable plunger or a movable seal in fluid communication with the lumen. The movable plunger or the movable seal provides a gas-tight seal. The movable plunger or the movable seal is configured and arranged for adjusting to changes in volume of the lumen when the lumen is filled with an acoustically-favorable medium and sealed. The imaging core is configured and arranged for inserting into the sealable lumen and for coupling to a control module.

In another embodiment, an intravascular ultrasound imaging system includes a catheter, an imaging core, and a control module. The catheter has a longitudinal length, a distal end, and a proximal end. The catheter includes a sealable lumen extending along the longitudinal length of the catheter from the proximal end to the distal end, and a movable plunger or a movable seal in fluid communication with the lumen. The movable plunger or the movable seal provides an acoustically-favorable-medium-tight seal. The movable plunger or the movable seal is configured and arranged for adjusting to changes in volume of the lumen to maintain an acoustically-favorable-medium-filled environment within the lumen when the lumen is filled with an acoustically-favorable medium and sealed. The imaging core is disposed within the lumen. The control module is coupled to the imaging core. The control module includes a pulse generator and a processor. The pulse generator and the processor are both electrically coupled to the imaging core. The pulse generator is configured and arranged for providing electric pulses to the imaging core. The processor is configured and arranged for processing received electrical pulses from the imaging core to form at least one image.

In yet another embodiment, a method for forming a catheter of an intravascular ultrasound imaging system includes degassing a sealable lumen of the catheter, filling the sealable lumen with an acoustically-favorable medium through at least one flush port, and sealing the lumen using a movable plunger or a movable seal in fluid communication with the sealable lumen. The catheter includes at least one transducer mounted to a driveshaft extending along at least a portion of a longitudinal length of the sealable lumen. The movable plunger or the movable seal is configured and arranged to adjust to changes in volume of the lumen to maintain the substantially degassed environment in the lumen.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular ultrasound imaging systems and methods of making and using the systems. The present invention is also directed to an intravascular ultrasound imaging system with a catheter having a sealed lumen filled with an acoustically-favorable medium, as well as methods of making and using the catheter and intravascular ultrasound system.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated by reference.

Figure 1:
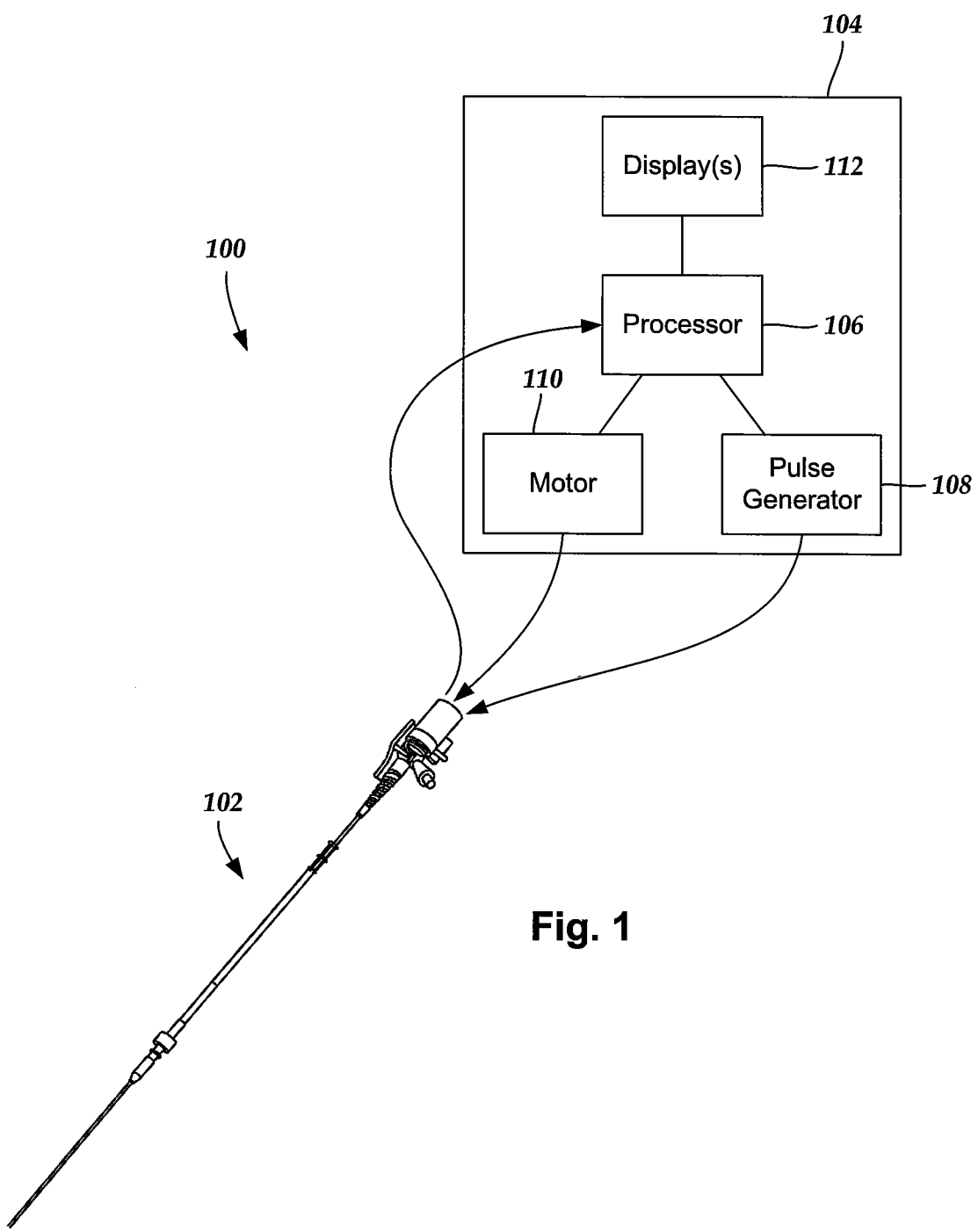
FIG. 1 is a schematic view of one embodiment of an intravascular ultrasound imaging system, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a motor 110, and one or more displays 112. In at least some embodiments, the pulse generator 108 forms electric pulses that may be input to one or more transducers (312 in FIG. 3) disposed in the catheter 102. In at least some embodiments, mechanical energy from the motor 110 may be used to drive an imaging core (306 in FIG. 3) disposed in the catheter 102. In at least some embodiments, electric pulses transmitted from the one or more transducers (312 in FIG. 3) may be input to the processor 106 for processing. In at least some embodiments, the processed electric pulses from the one or more transducers (312 in FIG. 3) may be displayed as one or more images on the one or more displays 112. In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the motor 110, the velocity or length of the pullback of the imaging core (306 in FIG. 3) by the motor 110, or one or more properties of one or more images formed on the one or more displays 112.

Figure 2:
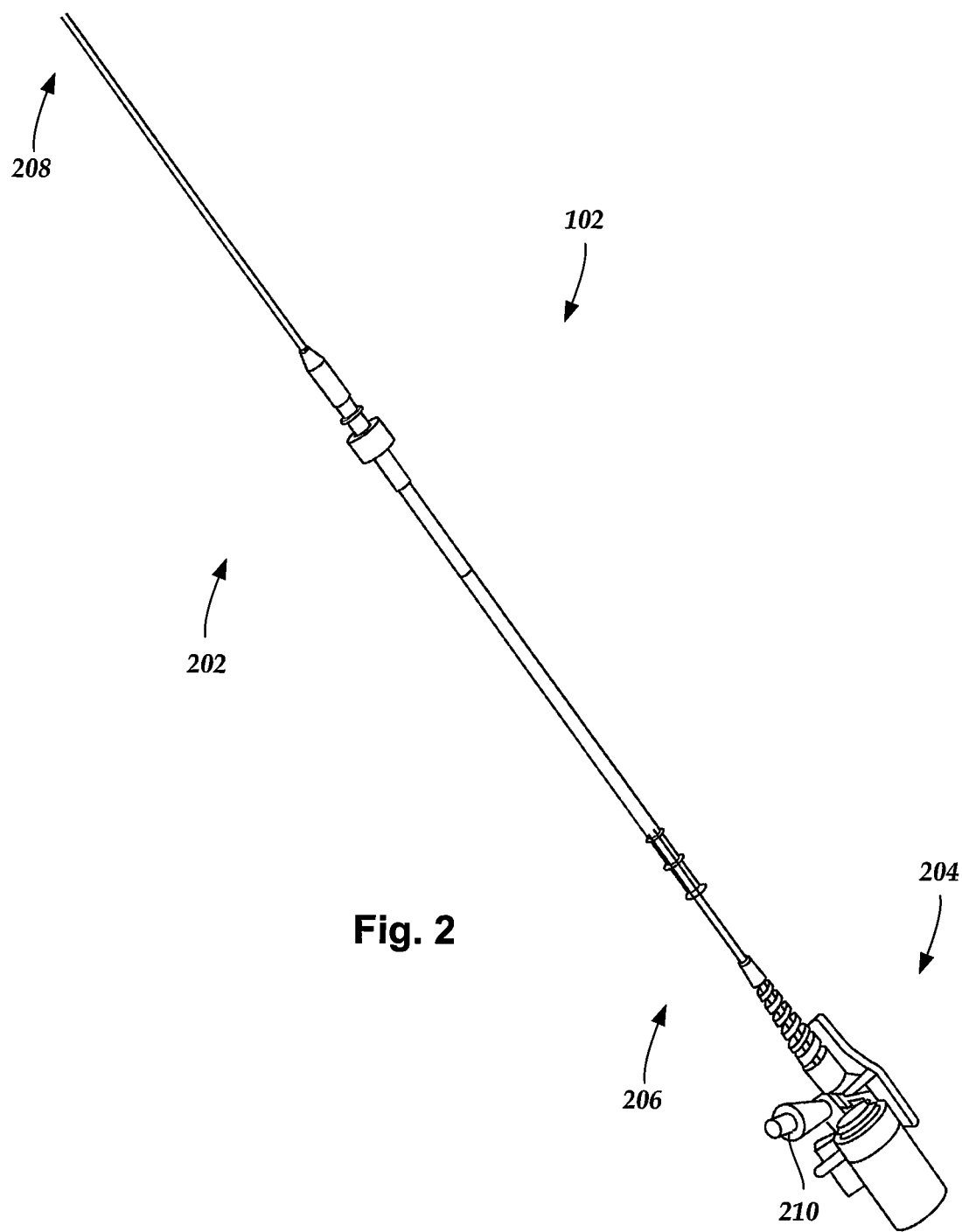
FIG. 2 is a schematic side view of one embodiment of a catheter of an intravascular ultrasound imaging system, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
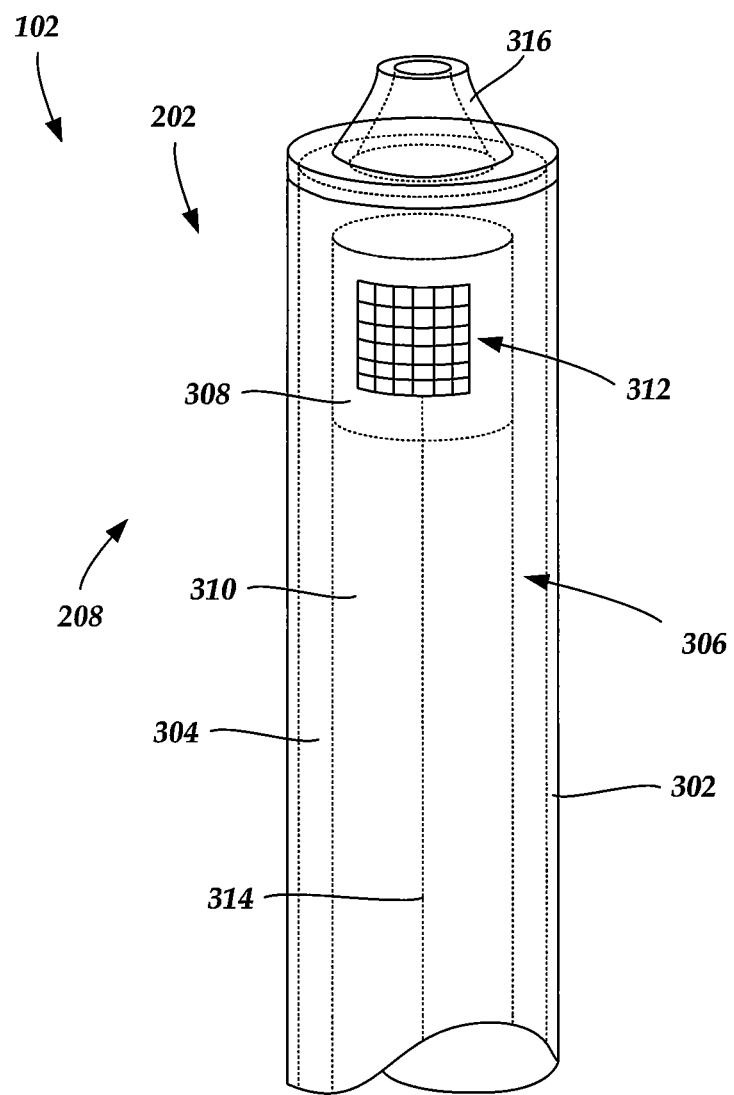
FIG. 3 is a schematic perspective view of one embodiment of a distal end of an elongated member of the catheter shown in FIG. 2 with an imaging core disposed in a lumen in the distal end of the elongated member, according to the invention.

FIG. 3 is a schematic perspective view of one embodiment of the distal end 208 of the elongated member 202 of the catheter 102. The elongated member 202 includes a sheath 302 and a lumen 304. An imaging core 306 is disposed in the lumen 304. The imaging core 306 includes an imaging device 308 coupled to a distal end of a rotatable driveshaft 310.

The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device 308 and employed to transmit and receive acoustic pulses. In a preferred embodiment (as shown in FIG. 3), an array of transducers 312 are mounted to the imaging device 308. In other embodiments, a single transducer may be employed. In yet other embodiments, multiple transducers in an irregular-array may be employed. Any number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic pulses.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

In at least some embodiments, the imaging core 306 may be rotated about a longitudinal axis of the catheter 102. As the imaging core 306 rotates, the one or more transducers 312 emit acoustic pulses in different radial directions. When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the motor 110 disposed in the control module (104 in FIG. 1).

As the one or more transducers 312 rotate about the longitudinal axis of the catheter 102 emitting acoustic pulses, a plurality of images are formed that collectively form a radial cross-sectional image of a portion of the region surrounding the one or more transducers 312, such as the walls of a blood vessel of interest and the tissue surrounding the blood vessel. In at least some embodiments, the radial cross-sectional image can be displayed on one or more displays 112.

In at least some embodiments, the imaging core 306 may also move longitudinally along the blood vessel within which the catheter 102 is inserted so that a plurality of cross-sectional images may be formed along a longitudinal length of the blood vessel. In at least some embodiments, during an imaging procedure the one or more transducers 312 may be retracted (i.e., pulled back) along the longitudinal length of the catheter 102. In at least some embodiments, the catheter 102 includes at least one telescoping section that can be retracted during pullback of the one or more transducers 312. In at least some embodiments, the motor 110 drives the pullback of the imaging core 306 within the catheter 102. In at least some embodiments, the motor 110 pullback distance of the imaging core is at least 5 cm. In at least some embodiments, the motor 110 pullback distance of the imaging core is at least 10 cm. In at least some embodiments, the motor 110 pullback distance of the imaging core is at least 15 cm. In at least some embodiments, the motor 110 pullback distance of the imaging core is at least 20 cm. In at least some embodiments, the motor 110 pullback distance of the imaging core is at least 25 cm.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 60 MHz.

In at least some embodiments, one or more conductors 314 electrically couple the transducers 312 to the control module 104 (See FIG. 1). In at least some embodiments, the one or more conductors 314 extend along a longitudinal length of the rotatable driveshaft 310.

In at least some embodiments, the catheter 102 with one or more transducers 312 mounted to the distal end 208 of the imaging core 308 may be inserted percutaneously into a patient via an accessible blood vessel, such as the femoral artery, at a site remote from the selected portion of the selected region, such as a blood vessel, to be imaged. The catheter 102 may then be advanced through the blood vessels of the patient to the selected imaging site, such as a portion of a selected blood vessel.

Acoustic pulses propagating from the one or more transducers 312 propagate through the lumen of the catheter 102 before passing through the sheath 302 to the region exterior of the catheter 102, such as a blood vessel or a chamber of a heart. Likewise, echo pulses reflected back to the one or more transducers 312 from medium boundaries also propagate through the lumen of the catheter 102. Typically, air is not a desirable transmission medium and image quality may, consequently, be reduced when acoustic pulses or echo pulses are required by catheter design to propagate through air. In the MHz range, acoustic pulses may not propagate at all through air. Accordingly, it is typically advantageous, and in some cases necessary, to purge air from the lumen 304 surrounding the one or more transducers 312 prior to the performance of an imaging procedure. One technique for purging air surrounding the one or more transducers 312 is to flush the lumen 304 with an acoustically-favorable medium through which acoustic pulses more easily propagate than through air Acoustically-favorable media may include one or more solvents such as, for example, water. An acoustically-favorable medium may include one or more solutes mixed with the one or more solvents such as, for example, one or more salts. In at least some embodiments, one or more agents may also be added, for example, to decrease the potential advancement of corrosion or microbial growth. In at least some embodiments, an acoustically-favorable medium may include a gel, and the like. In at least some embodiments, the acoustically-favorable medium may be input through the main flush port 210. In at least some embodiments, the elongated member 202 also defines an output port 316 for outputting one or more gases.

When using a conventional IVUS imaging system, a lumen of a catheter may be flushed to remove air at the beginning of an IVUS imaging procedure. Additionally, the lumen of the catheter may also need to be flushed of air one or more additional times during the course of the IVUS imaging procedure. Unfortunately, each flushing of air from the catheter lumen can add to the amount of time it takes for a healthcare professional to perform an IVUS imaging procedure on a patient. Moreover, the use of IVUS imaging systems often results in changes in volume of the lumen. For example, the volume of the lumen may change as the lumen twists and turns around tortuous blood vessels during placement of a catheter. Additionally, during an IVUS imaging procedure the volume of a lumen may change during pullback, as the imaging core 306 moves longitudinally along a longitudinal length of the catheter 102. As discussed above, in at least some embodiments the catheter 102 may include one or more telescoping sections that retract during pullback. In at least some embodiments, the retraction of the one or more telescoping sections may change the volume of the lumen. When the volume of a lumen changes, it may be the case that an air pocket develops across a portion of the path along which an acoustic pulse or an echo pulse propagates, thereby potentially reducing the quality of the IVUS image, or even prohibiting the IVUS imaging system 100 from forming an IVUS image.

Figure 4:
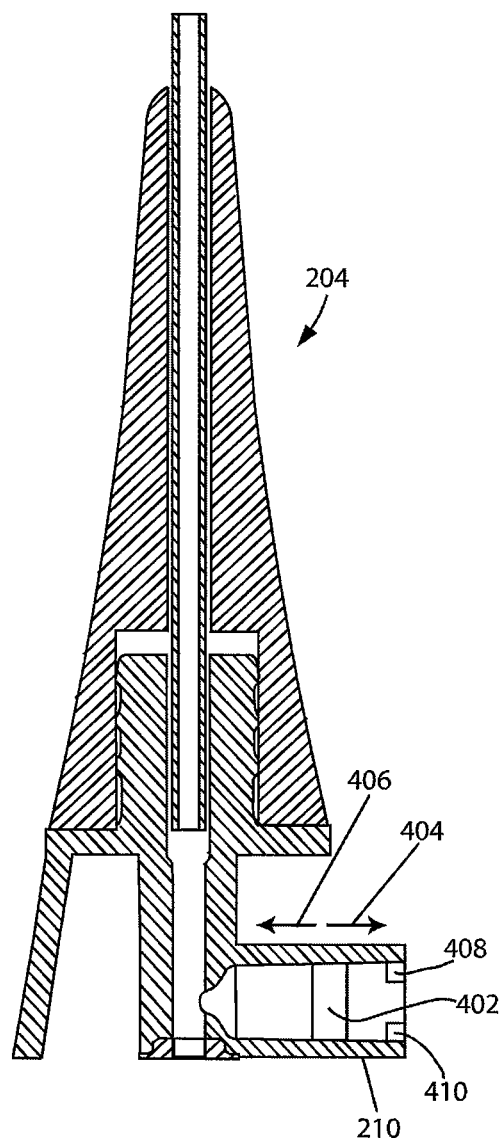
FIG. 4 is a schematic longitudinal cross-sectional view of one embodiment of a hub of a catheter, the hub including a movable plunger disposed in a main flush port, according to the invention.

To address these issues, in at least some embodiments the catheter 102 is filled with an acoustically-favorable medium and sealed so that the acoustically-favorable medium remains in the lumen 304. By sealing the catheter 102 with an acoustically-favorable medium, it is not necessary to flush the lumen 304 of air either before or during an IVUS imaging procedure. In at least some embodiments, the catheter 102 utilizes one or more movable seals or movable plungers in fluid communication with the lumen 304. The one or more movable seals or the movable plungers adjust to changes in the internal volume of the lumen 304 to maintain the lumen 304 of the catheter 102 filled with the acoustically-favorable medium. FIG. 4 is a schematic longitudinal cross-sectional view of one embodiment of the hub 204. The hub 204 includes a movable seal or a movable plunger 402 disposed in the main flush port 210. In at least some embodiments, the movable seal or the movable plunger 402 act like a piston moving up and down as the volume of the lumen 304 changes.

In at least some embodiments, the lumen 304 is degassed, filled with an acoustically-favorable medium, and sealed with the movable seal or the movable plunger 402. In at least some embodiments, degassing involves generating a vacuum in the lumen 304 and then filling the lumen 304 with an acoustically-favorable medium without introducing gas into the lumen 304. For example, in at least some embodiments, air in the lumen 304 is flushed out of the main flush port 210, an acoustically-favorable medium is input to the main flush port 210, and the main flush port 210 is sealed with the movable seal or the movable plunger 402. In at least some embodiments, the lumen 304 is degassed, filled with the acoustically-favorable medium, and the main flush port 210 is sealed all in one integrated step. In at least some embodiments, the operability of the imaging core 306 may be tested prior to sealing the main flush port 210.

Once the lumen 304 is filled with the acoustically-favorable medium and the main flush port 210 is sealed, the movable seal or the movable plunger 402 moves along a longitudinal length of the main flush port 210 in a direction shown by directional arrow 404 when the volume of the lumen 304 decreases. Conversely, when the volume of the lumen 304 increases, the movable seal or the movable plunger 402 moves in a direction shown by directional arrow 406. In at least some embodiments, each seal in fluid contact with the lumen 304 is provided with a vacuum seal.

In at least some embodiments, the volume of the main flush port 210 should be sufficient to allow the movable seal or the movable plunger 402 full movement for volume changes. In at least some embodiments, the movement of the movable seal or the movable plunger 402 may be restricted to a given longitudinal movement, thereby corresponding to a given volume. For example, in at least some embodiments, one or more stops may be used to limit the longitudinal movement of the movable seal or the movable plunger 402 within the main flush port 210. In FIG. 4, stops 408 and 410 are shown for limiting the movement of the movable seal or the movable plunger 402 in the direction shown by the directional arrow 404. In other embodiments, additional stops may be employed instead of, or in addition to, the stops 408 and 410 to limit the movement of the movable seal or the movable plunger 402 in the direction shown by the directional arrow 406.

In at least some embodiments, air in the lumen 304 is flushed out of the output port 316 and an acoustically-favorable medium is input to the main flush port 210. Once the air is removed from the lumen 304 and the acoustically-favorable medium is input to the main flush port 210, the output port 316 may be sealed with a fixed seal. In some embodiments, the fixed seal is made permanent, for example, by fusing the output port 316 or plugging the output port 316 with a cap and applying epoxy around the edges of the cap. In other embodiments, the fixed seal is designed to be removable. In at least some embodiments, the output port 316 is sealed with a vacuum seal. In at least some embodiments, the lumen 304 is degassed, filled with the acoustically-favorable medium, and the main flush port 210 and the output port 316 are sealed all in one integrated step. In at least some embodiments, the imaging core 306 may be tested for operability prior to sealing the main flush port 210 and the output port 316.

Figure 5A:
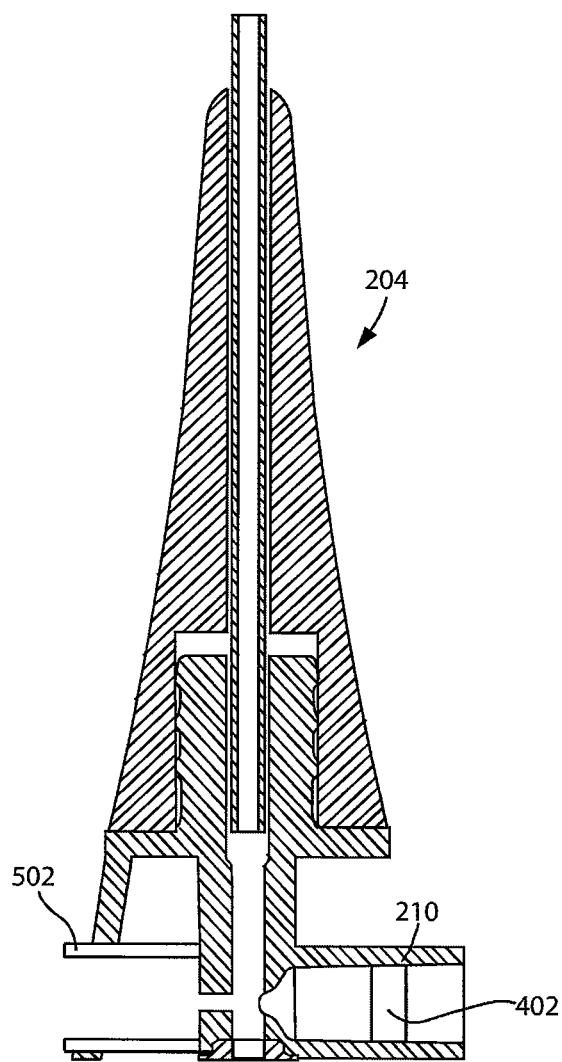
FIG. 5A is a schematic longitudinal cross-sectional view of one embodiment of a hub with a movable seal or a movable plunger disposed in a main flush port and an open auxiliary input port, according to the invention.

In at least some embodiments, the catheter 102 may also define one or more auxiliary ports. For example, in at least some embodiments, the catheter 102 may define one or more auxiliary flush ports. FIG. 5A is a schematic longitudinal cross-sectional view of one embodiment of the hub 204. The hub 204 defines the main flush port 210 and an auxiliary flush port 502. In FIG. 5A, the movable seal or the movable plunger 402 is shown disposed in the main flush port 210 and the auxiliary flush port 502 is shown open.

In at least some embodiments, the movable seal or the movable plunger 402 may be disposed in the main flush port 210 and the auxiliary flush port 502 may be used to degas or flush the air out of the lumen 304, as described above. Once the lumen 304 is degassed and filled with an acoustically-favorable medium, the auxiliary flush port 502 may be sealed with a fixed seal (either permanent or removable), as described above. In at least some embodiments, the auxiliary flush port 502 is sealed with a vacuum seal.

Figure 5B:
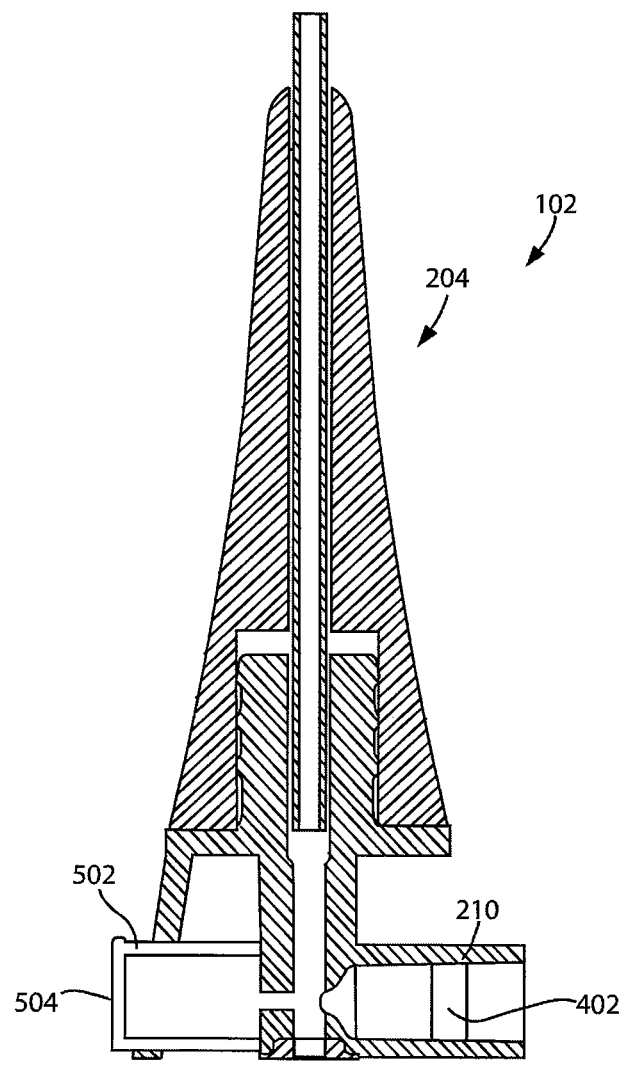
FIG. 5B is a schematic longitudinal cross-sectional view of another embodiment of a hub with a movable seal or a movable plunger disposed in a main flush port and a seal disposed in an auxiliary input port, according to the invention.

FIG. 5B is a schematic longitudinal cross-sectional view of one embodiment of the hub 204 with the movable seal or the movable plunger 402 disposed in the main flush port 210 and a fixed seal 504 disposed in the auxiliary flush port 502. In at least some embodiments, the movable seal or the movable plunger 402 is disposed in the auxiliary flush port 502 and the fixed seal 504 is disposed in the main flush port 210. In at least some embodiments, a plurality of auxiliary flush ports are defined by the catheter 102. In at least some embodiments, the fixed seal 504 or the movable seal or the movable plunger 402 is disposed in each of the auxiliary flush ports.

In at least some embodiments, one or more auxiliary output ports are defined in the catheter 102. In at least some embodiments, the movable seal or the movable plunger 402 is disposed in the output port 316. In at least some embodiments, the movable seal or the movable plunger 402 is disposed in one or more auxiliary output ports. In at least some embodiments, the movable seal or the movable plunger 402 is disposed in a reservoir in fluid communication with one or more of the main flush port 210, the one or more of the auxiliary flush ports 502, the output port 316, or the one or more auxiliary output ports.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for forming a catheter of an intravascular ultrasound imaging system, the method comprising:
   degassing a sealable lumen of the catheter, the catheter further comprising at least one telescoping section configured and arranged for extension and retraction and at least one transducer mounted to a driveshaft extending along at least a portion of a longitudinal length of the sealable lumen;
   filling the sealable lumen with an acoustically-favorable medium through at least one flush port; and
   sealing the lumen using a movable plunger or a movable seal in fluid communication with the sealable lumen, the movable seal or movable plunger configured and arranged to automatically adjust position in response to changes in volume of the lumen, including changes in the volume of the lumen due to extension or retraction of the at least one telescoping section, to maintain a substantially degassed environment in the lumen.

2. The method of claim 1, wherein sealing the lumen using the movable plunger or the movable seal in fluid communication with the sealable lumen comprises disposing the movable plunger or the movable seal in one of the at least one flush port.

* * * * *